US008679168B2

(12) United States Patent  (10) Patent No.: US 8,679,168 B2
McNamara et al.  (45) Date of Patent: Mar. 25, 2014

(54) CANNULATED ANCHOR AND SYSTEM

(75) Inventors: Michael G. McNamara, Anchorage, AK (US); Avery B. Munoz, Eagle River, AK (US)

(73) Assignee: Alaska Hand Research, LLC, Anchorage, AK (US)

(*) Notice: Subject to any disclaimer, the term of this patent is extended or adjusted under 35 U.S.C. 154(b) by 675 days.

(21) Appl. No.: 12/395,891

(22) Filed: Mar. 2, 2009

(65) Prior Publication Data
US 2010/0076499 A1 Mar. 25, 2010

Related U.S. Application Data

(60) Provisional application No. 61/067,911, filed on Mar. 3, 2008.

(51) Int. Cl.
*A61B 17/04* (2006.01)
*A61B 17/86* (2006.01)
*A61F 2/08* (2006.01)

(52) U.S. Cl.
USPC ............ 606/308; 606/304; 606/305; 606/232

(58) Field of Classification Search
USPC .......................................... 606/232, 300–321
See application file for complete search history.

(56) References Cited

U.S. PATENT DOCUMENTS

| 5,423,819 | A | 6/1995 | Small et al. |
|---|---|---|---|
| 5,584,836 | A | 12/1996 | Ballintyn et al. |
| 5,690,676 | A | 11/1997 | DiPoto et al. |
| 5,718,706 | A | 2/1998 | Roger |
| 5,944,724 | A | 8/1999 | Lizardi |
| 6,139,565 | A | 10/2000 | Stone et al. |
| 6,280,474 | B1 | 8/2001 | Cassidy et al. |
| 6,517,564 | B1 | 2/2003 | Grafton et al. |
| 6,524,317 | B1 | 2/2003 | Ritchart et al. |
| 6,554,852 | B1 | 4/2003 | Oberlander |
| 6,569,188 | B2 * | 5/2003 | Grafton et al. ............... 606/232 |
| 6,685,728 | B2 | 2/2004 | Sinnott et al. |
| 6,840,953 | B2 | 1/2005 | Martinek |
| 7,226,469 | B2 | 6/2007 | Benavitz et al. |
| 7,235,079 | B2 | 6/2007 | Jensen et al. |
| 7,588,587 | B2 | 9/2009 | Barbieri et al. |
| 2002/0022862 | A1 | 2/2002 | Grafton et al. |

(Continued)

FOREIGN PATENT DOCUMENTS

| WO | WO97/30649 A1 | 8/1997 |
|---|---|---|
| WO | WO03/063713 A1 | 8/2003 |
| WO | WO2006/088359 A1 | 8/2006 |
| WO | WO2006/099109 A2 | 9/2006 |

*Primary Examiner* — Andrew Yang
*Assistant Examiner* — Olivia C Chang
(74) *Attorney, Agent, or Firm* — Law Office of Herbert A. Newborn

(57) ABSTRACT

Cannulated anchors are provided that may be optimally forced in, press fit, screwed in or otherwise installed into tissue with minimal damage to the flexible members or sutures attached thereto. Systems for installing at least one flexible member into tissue include the cannulated anchor, the at least one flexible member capable of being received by the cannulated anchor; and an installer with a driver head insertable into the cannulation of the anchor proximate the trailing end and with an essentially longitudinal cannulation centrally disposed along the axis and sized to accept a guidewire therethrough. Movement of the installer about the longitudinal axis causes corresponding movement of the cannulated anchor such that the outer surface of the cannulated anchor is capable of effecting anchoring into the tissue.

50 Claims, 6 Drawing Sheets

(56) References Cited

U.S. PATENT DOCUMENTS

| | | | |
|---|---|---|---|
| 2003/0167072 A1* | 9/2003 | Oberlander | 606/232 |
| 2004/0153074 A1 | 8/2004 | Bojarski | |
| 2005/0283158 A1* | 12/2005 | West | 606/73 |
| 2006/0189993 A1 | 8/2006 | Stone | |
| 2007/0191708 A1 | 8/2007 | Gerold et al. | |
| 2007/0213730 A1 | 9/2007 | Martinek et al. | |
| 2007/0292820 A1* | 12/2007 | Canter | 433/173 |
| 2008/0140118 A1 | 6/2008 | Martinek | |
| 2008/0147063 A1 | 6/2008 | Cauldwell et al. | |
| 2008/0243184 A1 | 10/2008 | Martinek et al. | |

* cited by examiner

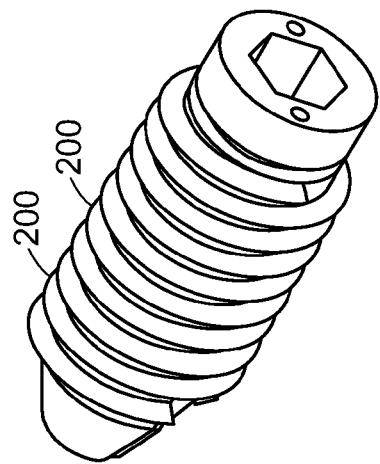
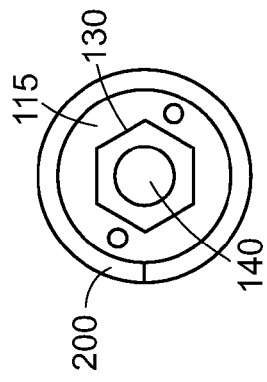
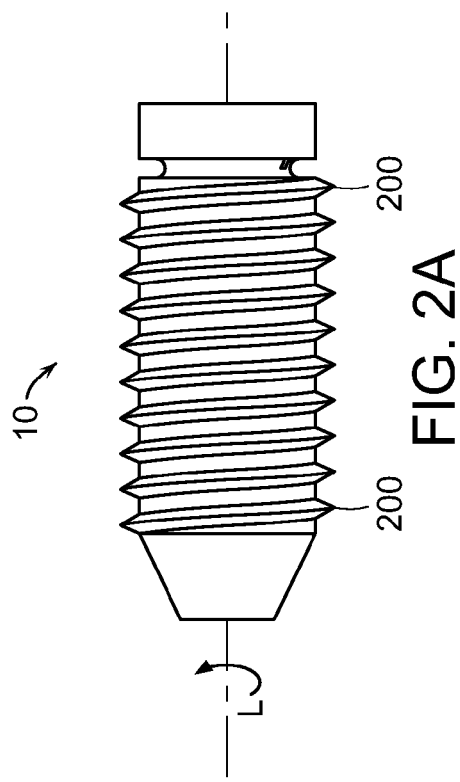
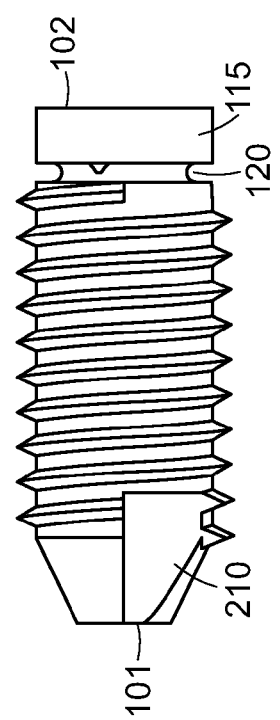

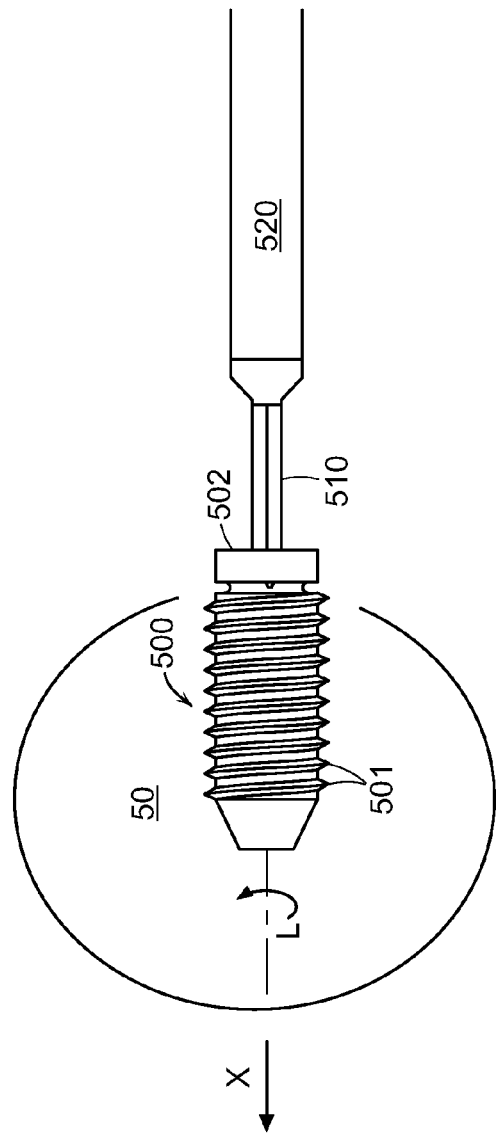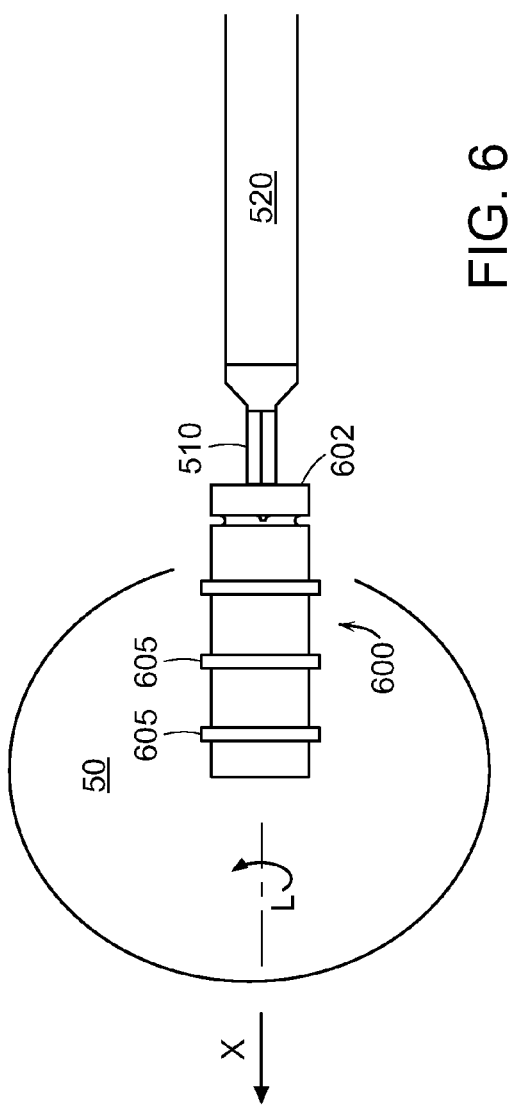

CANNULATED ANCHOR AND SYSTEM

This application claims the benefit of U.S. Provisional Patent Application Ser. No. 61/067,911, filed Mar. 3, 2008, which is incorporated herein by reference.

TECHNICAL FIELD

The present invention relates to implantable medical devices, and more specifically, to a system for securing flexible members/sutures with tissue.

BACKGROUND ART

Suture anchors are commonly used in orthopedic surgery to affix suture to bone. Sutures may then be affixed to tissue or a secondary implant, thereby securing the tissue or device to bone. Often, the suture anchor is used to repair an injured tendon or ligament. Alternatively, the anchor may be installed alongside an autograft, allograft, xenograft or synthetic tissue implant using interference to secure the material within a bone tunnel.

External features along the anchor body are known in the art for effecting engagement of a suture anchor with tissue. Examples of these features, which may be used combination, include self-tapping helical ridges and cutting flutes for threaded engagement with bone and conical protuberances or deployable barbs for pound-in bone engagement. Anchors may be composed of any suitable biocompatible absorbable or non-absorbable material. Factors determining selection of an anchor include personal preference with regards to material or method of engagement with bone (pound-in versus screw-in), bone quality at the surgical site, plans for removal or revision surgery, or unique requirements of a particular surgical procedure.

High-strength suture is readily available (FiberWire®, Orthocord™) and often coupled with anchors for use in orthopedic surgery. Many suture anchors currently available on the market rely upon the characteristic tensile strength and resistance to breakage of these sutures, given small eyelets allowing for high contact pressures along the length of a strand, interference between suture and external anchor features, and abrasion with a bone tunnel during insertion. However, recent publications have shown that these sutures can cause damage to surrounding bodily tissue, and surgeons may question usage of anchors utilizing them. Whereas conventional sutures are not as durable as the high-strength counterparts, it is desirable to provide an anchor with a flexible member/suture attachment capable of protecting the member from contact with bone or potentially damaging anchor features.

Research suggests that broader tissue insertion leads to better surgical outcomes than do the center-point attachment provided by many anchors and systems currently on the market. It is believed that an improved anchor design would allow for flexible member/suture strands to extend from locations proximate the outer diameter of the device, rather than from a centrally located eyelet.

Many devices, viewed from an installer end and looking towards an anchor at a leading end, taper or reduce in diameter from largest to smallest. Other anchors have a flange or head at a trailing end that secures the anchor within a near cortex of a bone or holds a soft tissue against bone. There is a need for, and the inventors are unaware of, a cannulated suture anchor capable of being loaded onto a guidewire and engaged with the driver head of a cannulated installer, the anchor subsequently moved by the installer longitudinally along the guidewire to the far cortex of a bone, across an intra-articular space for engagement into a second bone or across a fracture.

SUMMARY OF THE INVENTION

Embodiments of the present invention solve problems of the prior art with respect to maximizing the accuracy of anchor placement and anchor alignment in tissue. Embodiments provide anchors that may be optimally forced in, press fit, screwed in or otherwise installed into tissue with minimal damage to the flexible members attached thereto. Such embodiments, having an inner core portion and an outer portion may be fabricated integrally. Alternatively, inner core portions may be manufactured to be compatible with different outer portions, subsequently attached thereto; the various outer portions capable of effecting anchoring by force, press fit, screw in, or other known methodologies.

Additional embodiments further provide for the incorporation of radio-opaque material to monitor anchor movement after installation without the need for reopening the site. For instance, when a revision surgery or removal of an implant is not desired or required, a cannulated anchor embodiment may have a porous coating disposed thereon for enhanced osseointegration. Systems and methods utilizing the anchors are also provided.

Accordingly, in an embodiment, a cannulated anchor as part of a system for installing at least one flexible member into tissue is provided. The anchor includes an essentially cylindrical inner core anchor portion having an inner core exterior wall and having an inner core length defined along a longitudinal system axis, the inner core length extending between a leading end and a trailing end. The inner core anchor portion has a cannulation centrally disposed along the axis, the cannulation sized to accept a guidewire therethrough along the inner core length, the cannulation sized to engage an installer therethrough along a trailing portion of the inner core length. The inner core anchor portion also includes at least one recess disposed circumferentially within the inner core exterior wall, the at least one recess sized to accept a recess portion of the at least one flexible member. The inner core anchor portion also has a plurality of channels, each channel disposed essentially along the axis, each channel extending from the trailing end and in communication with the at least one recess, each channel sized to accept a channel portion of the at least one flexible member. The anchor also has an outer anchor portion having an outer length defined along the system axis and an outer surface, such that the outer surface is capable of effecting anchoring of the cannulated anchor into the tissue. Note that the inner core anchor portion itself is provided as another embodiment of the present invention.

The plurality of channels are sized and located within the maximum diameter of the inner core anchor portion so as to prevent abrasion of a flexible member(s)/suture strand(s) with tissue or an external feature along the body of the anchor. The plurality of channels may be beneficially isolated entirely from the cannulation along the trailing portion of the core length so as to prevent any migration of a suture into the cannulation. This would greatly minimize harmful interference between the driver head of an installer and the flexible member when the driver head is mounted in the cannulation.

The outer anchor portion may also have a plurality of helical ribs, each rib disposed at a particular outer length position, each outer length position disposed between a first axial location proximate to the trailing end and a second axial location proximate to the leading end. The plurality of helical ribs may be configured to provide threaded engagement with bone, as is known to one of ordinary skill in the art.

Further embodiments may have a cannulation having a trailing profile (i.e. a profile disposed only along the trailing portion of the core length) sized and dimensioned for matching with a driver head of an installer. The cannulation may have a hexagonal profile along the trailing portion of the inner core length. The profile can be of any shape and still considered to be within the spirit of the invention if it is configured to match that of the driver head of the installer. Each of the plurality of channels may be aligned with a trailing feature of the inner core anchor portion. For example, in the case of a hexagonal trailing cannulation profile, each channel may be aligned with a side of that profile.

The at least one recess of the cannulated anchor may have a recess arc length measurable in circumferential degrees about the inner core anchor portion. Arc lengths of 180 or 360 degrees may be beneficial depending on the surgical situation. The at least one recess of the cannulated anchor might also have a recess arc length of less than 10 degrees wherein the at least one recess is sized to accept a knotted portion of the at least one flexible member.

A portion of the cannulated anchor may be radio-opaque; the body of the anchor may be treated with a porous coating for osseointegration The cannulated anchor may have a maximum diameter, the maximum diameter larger than an inner core anchor portion diameter; such that the outer surface is capable of effecting anchoring into the tissue when the cannulated anchor is forced into tissue essentially along the axis.

In yet another embodiment, a system for installing at least one flexible member into tissue, is provided: The system includes the cannulated anchor of previous embodiments, the at least one flexible member capable of being received by the cannulated anchor; and an installer with a driver head insertable into the cannulation of the anchor proximate the trailing end and with an essentially longitudinal cannulation centrally disposed along the axis and sized to accept a guidewire therethrough. Movement of the installer about the longitudinal axis causes corresponding movement of the cannulated anchor such that the outer surface of the cannulated anchor is capable of effecting anchoring into the tissue. The trailing profile of the inner core anchor cannulation may, beneficially, be matched with the driver head of the installer.

In a further embodiment, a method for installing at least one flexible member into tissue is provided. The method includes inserting a guidewire into the tissue, engaging the installer with the cannulated anchor of previous embodiments, positioning the anchor and installer over the guidewire, and moving the installer causing corresponding movement of the anchor, such that the outer surface of the cannulated anchor is capable of effecting anchoring into the tissue.

Methods are also provided for installing a flexible member across a first bone, across an intra-articular space and into a second bone. Methods include inserting a guidewire into a first bone, advancing the guidewire across an intra-articular space and into a second bone, engaging an installer with the cannulated anchor of previous embodiments, positioning the anchor and installer over the guidewire, moving the installer causing corresponding movement of the anchor, and moving the anchor across the intra-articular space to engage the anchor in the second bone. Further embodiments specifically provide methods of advancing an anchor that has its outer surface configured for threaded engagement with tissue and bone.

BRIEF DESCRIPTION OF THE DRAWINGS

FIG. 2(a)-(d) depict various views of a "screw-in" embodiment of a cannulated anchor comprising the inner core anchor portion of FIG. 1(a)-(d) in accordance with an embodiment;

FIG. 5 schematically shows a side view of an embodiment of a system for installing a "screw-in" cannulated anchor;

FIG. 6 schematically shows a side view of an embodiment of a system for installing a "press-fit" cannulated anchor.

DETAILED DESCRIPTION OF SPECIFIC EMBODIMENTS

Figure 1C:
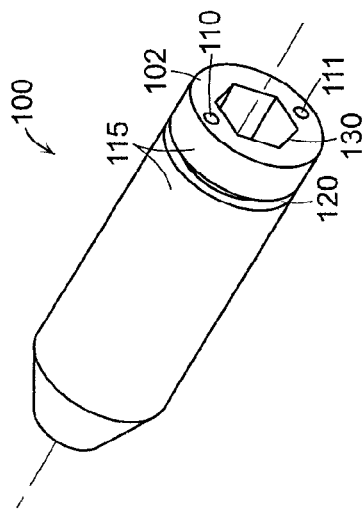
FIG. 1(a)-(d) depict various views of an inner core anchor portion in accordance with a first embodiment.
Figure 1D:
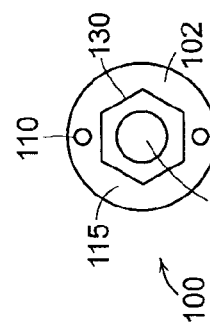

Regarding a first embodiment, with reference to FIG. 1(a)-(d), inner core anchor portion 100 is shown. Inner core anchor portion 100 has a leading end 101 and trailing end 102; ends 101 and 102 are determined with reference to a defined longitudinal system axis, L, along which cannulated anchor 10 is moved to engage and anchor into tissue. Inner core anchor portion 100, while being essentially cylindrical is, in the embodiment of FIG. 1(a)-(d), shown to be tapered proximate to leading end 101. There may be a variety of reasons to taper the inner core 100, notably for ease of insertion into a preexisting tissue orifice prepared by a cannulated drill. However, there are circumstances (as shown supra) for which tapering may be undesirable and is, therefore, not considered an essential feature of the disclosed cannulated anchor embodiments. Centrally disposed cannulation 130 is sized to accept a guidewire (not shown) therethrough. When viewing FIGS. 1(c) and 1(d) (as well as 1(a)), cannulation 130 is larger in size proximate trailing end 102 than it is proximate leading end 101. The portion of the cannulation proximate leading end 101 is sized to accommodate sliding of the anchor 10 over a guidewire (not shown) that is typically already accurately inserted, at its leading end, into tissue. In many procedures, particularly those in which superior positional accuracy and alignment of the anchor 10 are key factors for surgical success, the central disposition of the cannulation 130 in inner core anchor portion 100 insures optimal anchor placement and alignment based upon the previously accurate guidewire placement. FIG. 1(d), views inner core anchor portion 100 as the user would see it, particularly during arthroscopic surgery. The user views trailing end 102, sitting along axis L toward leading end 101 and toward the tissue insertion location. The circular (or, more generally, a matching shape of the guidewire profile) profile of cannulation 130 proximate leading end 101 is denoted in FIG. 1(d) as reference 140. The profile of cannulation 130 is shaped and sized to mechanically engage an installer with matching profile from an axial location that is a specific distance d along axis L (d, shown generically in FIG. 1(a), may vary for specific applications and procedures based upon particulars of the insertion tool ((not shown)) used) to trailing end 102. The trailing portion of cannulation 130 is shown in FIGS. 1(c) and 1(d) having a hexagonal profile to accommodate a hexagonally profiled inserter. This trailing profile 140 of the trailing portion of cannulation 130 may have any shape to match part or all of the profile of any suitable installer. This trailing portion of cannulation 130 may feature a suitable stop or catch 150 (shown generically in FIG. 1(a)) disposed proximate the axial location proximate to the specific distance d along axis L so that force applied to the installer is capable of being optimally transmitted to anchor 10. Design of such stop or catch 150 could be any design known to one of ordinary skill.

Figure 1A:
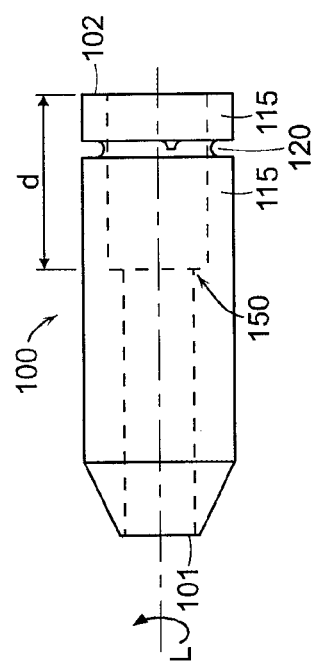
Figure 1B:
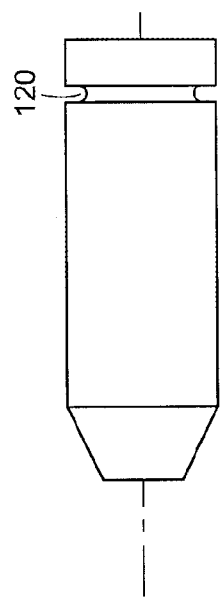

A pathway embodiment for at least one suture or other desired flexible member (suture/flexible member not shown) is illustrated in FIG. 1(a)-(d). In order to optimize the placement, alignment, and effective installation of anchor 10 and to minimize damage to the suture or flexible member, the pathway, in all of the disclosed embodiments herein, insures a degree of isolation of the suture/flexible member both from the cannulation 130 itself and from the interface to be created between anchor 10 and engaged tissue. Referring to FIG. 1(a)-(c), a pair of channels 110 are aligned essentially along axis L from trailing end 102 through inner core wall 115. Circumferential groove 120 is disposed on and forms a recess into inner core wall 115 and is in communication with channels 110. The pathway embodiment of FIG. 1(a)-(d) is such that the suture/flexible member would pass through first channel 110, enter groove 120, and exit inner core anchor portion 100, through second channel 111. Channels 110, 111 are appropriately sized to accept a channel portion of at least one flexible member. In the embodiment of FIG. 1(a)-(d) (and, in fact for all of the illustrative embodiments disclosed herewith), channels 110, 111 are shown to have a simple circular cross-section. Circularity is not a necessary feature of these channels; any shaped cross-section is considered to be in the spirit of this disclosure so long as the channels are sufficiently smooth to avoid fraying of, or other damage to, the suture/flexible member when it/they are tensioned.

In the embodiment of FIG. 1(a)-(d), circumferential groove 120, sized to accept a recess portion of at least one flexible member, is shown as a continuous groove with a curved profile. Any shaped recess is considered to be in the spirit of this disclosure so long as, once again, the recess is disposed within the inner core anchor portion 100 and is sufficiently smooth to avoid fraying or other damage to the suture or flexible member when it/they are installed in tissue and tensioned. Further, in this embodiment, groove 120 is cut into the entire circumference (i.e. the groove has a recess arc length of 360°). Alternatively, the pathway may be of a length that is from channel 110, halfway around the circumference and into channel 111. Alternatively, the pathway may be of a length measured to be an additional integral number of circumferences longer, thus including a number of wraps of the flexible suture/member around core anchor portion 100. In yet another variation, circumferential recess 120 might only extend halfway around the circumference of core anchor portion 100 (i.e. having only an 180° arc length).

In yet another variation of this embodiment, to accommodate users comfortable with or, otherwise preferring, knotted suture/flexible members, circumferential recess 120 may have a small circumferential arc length (e.g. less than about 10°) sufficient to receive a knotted member end of a first member. Channel 110 would still be sized as described infra, while recess 120 would be sized to accept the knotted end of the member. The knot would remain secured in recess 120 either frictionally or by a weld or other method known in the art, while the other, unknotted end of the member would be accessible to the user from trailing end 102. Similarly a second knotted member may have a pathway through channel 111 having its knotted end secured in circumferential recess 120. Although FIG. 1(a)-(d) illustrate only a pair of channels 110, 111, the variation using knotted sutures/flexible members could provide for the anchoring of numerous knotted members each of the members passing through its own distinct channel with each knotted end captured in a single recess 120 at distance d from trailing end 102 or from many recesses 120, each with less than a complete (i.e. 360°) circumferential arc length.

Referring now to FIG. 2(a)-(d), a cannulated anchor 10 embodiment is comprised of inner core anchor portion embodiment 100 shown in FIG. 1(a)-(d) and an outer anchor portion. The outer anchor portion of FIG. 2(a)-(d) features a plurality of helical ribs 200. Helical ribs 200 are disposed at outer anchor locations (or outer length positions) along axis L. These locations are shown to be disposed between the onset of the taper of inner core anchor portion 100 and circumferential recess 120. Helical ribs 200 extend radially outward from inner core wall 115. The ribs 200, along with cutting edge 210, provide an outer surface for cannulated anchor 10 that effects anchoring into tissue by rotating anchor 10 about axis L thereby creating a self-tapped orifice into tissue. Anchor 10 is, in effect, screwed into the tissue orifice created by rotating anchor 10. Rotation is accomplished by applying torque to an installer when engaged with anchor 10 via the placement of a portion (sometimes referred to as the head) of the installer into cannulation 130.

Figure 3C:
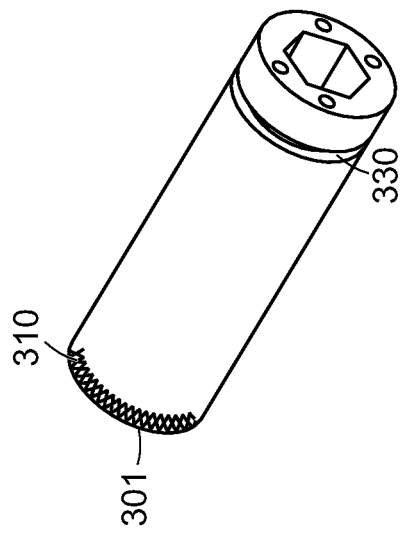
FIG. 3(a)-(d) illustrate various views of an inner core anchor portion in accordance with another embodiment.
Figure 3D:
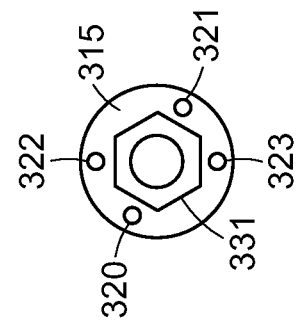
Figure 3A:
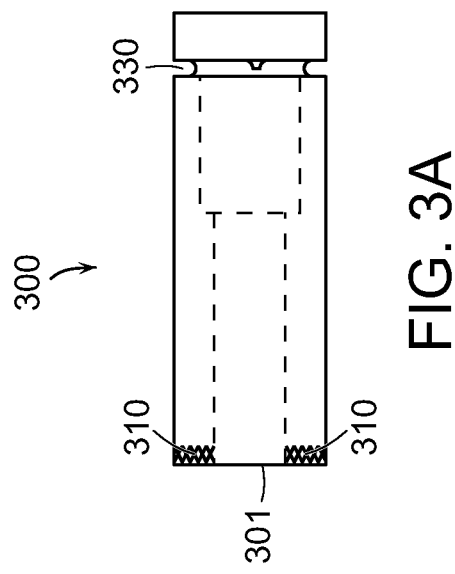
Figure 3B:
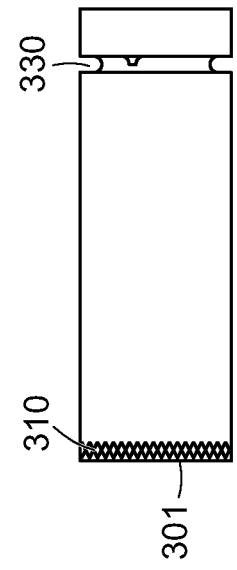
Figure 4C:
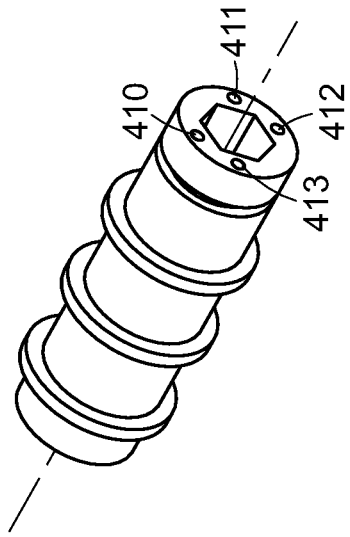
FIG. 4(a)-(d) illustrate various views of a "press-fit" embodiment of a cannulated anchor in accordance with a further embodiment.
Figure 4D:
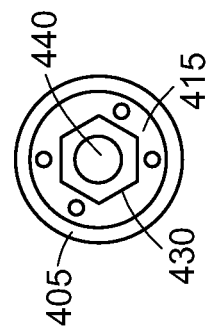
Figure 4A:
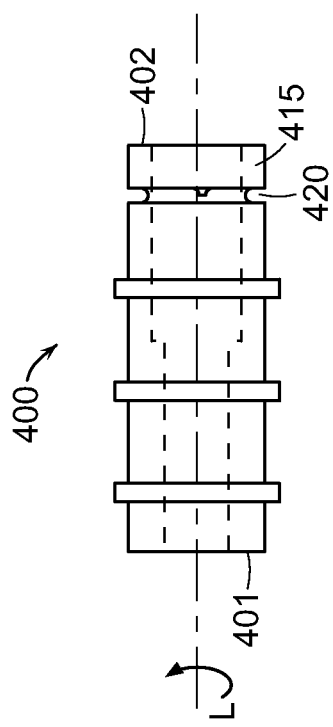
Figure 4B:
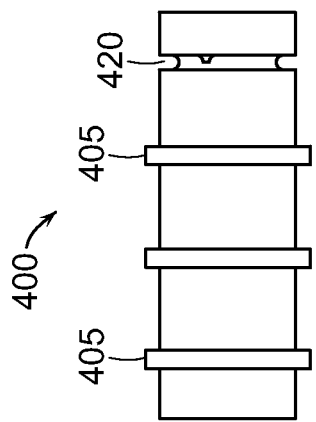

As previously mentioned, there are circumstances for which tapering of the leading end of an inner core anchor portion may be undesirable. FIG. 3(a)-(d) illustrates such an embodiment having untapered leading end 301. Two additional features are also illustrated in FIG. 3(a)-(d) (Note that these two features may be applied generically to other disclosed embodiments). First, inner core anchor portion 300 may be fabricated from metal, usually titanium or other biocompatible metal. Alternatively, inner core anchor portion 300 may be made from a bioabsorbable (or other) polymer. As anchors may tend to move with time following surgical completion, it is highly desirable to determine whether anchor movement has occurred without having to reopen the installation site. Therefore, radio-opaque material 310 is shown to be disposed at or near leading end 301. Such radio-opaque material may be beneficially included in any or all anchor embodiments. In the event that an anchor is to be permanently placed (without intentions for its removal during revision surgery), a porous coating may be beneficially included in any or all anchor embodiments to promote osseointegration. Second, FIG. 3(d) depicts two pairs (four in total) of flexible member channels 320, 322 and 321, 323. Each pair is disposed through inner core wall 315 and is in communication with circumferential groove or recess 330. In the embodiment of FIG. 3(a)-(d), circumferential groove 330, sized to accept a recess portion of at least one flexible member, is shown as a continuous groove with a curved profile. Groove 330 is shown cut into the entire circumference (i.e. the groove has a recess arc length of 360°). Flexible member pathway possibilities are numerous. For example, one pathway combination may be of a first length that is from channel 320, partially around the circumference and into channel 322 and a second length from channel 321, partially around the circumference and into channel 323. As described previously, groove 330 may be comprised of segments that are not cut completely around inner core wall 315. Alternatively (not shown), there may be multiple circumferential grooves cut around inner core wall 315, with pair(s) of channels in communication with a single, particular groove. Each of the grooves would then have recess arc lengths of less than 360° keyed about the circumference to the positions of the pair(s) of channels in communication. In yet another variation of this embodiment, to accommodate users comfortable with, or otherwise preferring, knotted suture/flexible members, circumferential recess 330 may consist of four small circumferential arc lengths (e.g. less than about 10°) sufficient to receive knotted member ends of four members. Embodiments are envisioned within the spirit of the present disclosure that may feature numerous channels disposed about inner core wall 315, accommodating numerous sutures/flexible members. Inner core anchor portions 300 having numerous such channels (e.g. 320) provide, in principle, effective anchor systems featuring improved accuracy and alignment in limited working space, optimized flexible member tissue installment with minimized chance of damage to the members so long as these receivable members remain isolated from both cannulation 331 and from the tissue-anchor interface during installation and operation.

In yet a further embodiment (refer to FIG. 4(a)-(d)), inner core anchor portion 400 has untapered leading end 401. Anchor 400 is shown with outer anchor portion 405 as a set of radial protrusions at axial locations along axis L. Surfaces of protrusions 405, barbs, or other variations known in the art are designed to render anchor 400 capable of effecting anchoring of the cannulated anchor 400 into the tissue. Anchor 400, in contrast to the previously disclosed embodiments that are designed to be screwed into a tissue orifice created by and/or modified by torquing anchor, is designed to be press fit or otherwise forced into a pre-existing tissue orifice. Channels 410-413 and circumferential recess/groove 420, cannulation 430, and cannulation portion 440 proximate leading end 401, are analogous in function and disposition to features of the other embodiments. Variations of the features (i.e. number of channels/grooves, length of/dimensions of cannulation portion 440, etc.) described for previous embodiments are also provided within the spirit of this disclosure. The receivable flexible members/sutures beneficially remain isolated from both cannulation 430 and from the tissue-anchor interface during installation and operation.

Referring now to FIG. 5, a cannulated anchor system of the "screw-in" variety is shown. Cannulated anchor 500 has been partially installed into tissue 50. Installer 510 is shown inserted and engaged in the cannulation of anchor 500. Grasper handle 520 is shown to be linked mechanically with installer 510 generally along axis L. Motion of handle 520 along L in direction x results in corresponding motion of installer 510 and corresponding motion of anchor 500. In particular, rotational motion of installer 510, results in corresponding rotation of anchor 500, the helical ribs/threads 501 disposed on the outer surface of anchor 500 being effective in cutting an appropriate orifice in tissue 50. In a particular methodology, installer 510 and grasper handle 520 are also cannulated so as to accept a guidewire (not shown in side view) through their respective cannulations. This facilitates accurate placement and alignment of the resulting installed anchor based upon previous guidewire placement and alignment. Suture(s)/flexible members will be accessible to the user extending out of trailing end 502 of anchor 500. After placement of anchor 500 in the orifice in tissue 50 created by the "screw-in" action, inserter 510, handle 520, and the guidewire (if still within the cannulation) are removed in the opposite direction from x. As has been stated previously, suture(s)/flexible member(s) are isolated from both the path of inserter 510 and from the cutting edges of the helical ribs/threads 501.

FIG. 6 illustrates a cannulated anchor system of the "press-fit," "force in," or "pound-in" variety. Cannulated anchor 600 has been partially installed into tissue 50. Installer 510 is shown inserted and engaged in the cannulation of anchor 600. Grasper handle 520 is shown to be linked mechanically with installer 510 generally along axis L. Motion of handle 520 along L in direction x results in corresponding motion of inserter 510 and corresponding motion of anchor 600. In this case, applied force upon inserter 510 (via force on handle 520) in direction x, results in corresponding motion of anchor 500, the radial protrusions 605 disposed on the outer surface of anchor 600 being effective in installing anchor 600 into a, perhaps, pre-existing orifice in tissue 50. In certain procedures, a method may include affixing a material into a pre-existing orifice in a bone using an anchor of any or all embodiments described herein. The cannulated anchor therefore functions as an interference anchor and may be used to secure any number of materials (autograft, allograft, xenograft or a synthetic) within a bone, as is known to one of ordinary skill in the art. In a particular methodology, installer 510 and grasper handle 520 are also cannulated so as to accept a guidewire (not shown in side view) through their respective cannulations. This facilitates accurate placement and alignment of the resulting installed anchor based upon previous guidewire placement and alignment. The guidewire may or may not remain within the cannulations during the forcing/press fitting operation. Suture(s)/flexible member(s) will be accessible to the user extending out of trailing end 602 of anchor 600. After placement of anchor 600 in the orifice in tissue 50, installer 510, handle 520, and the guidewire (if still within the cannulations) are removed in the opposite direction from x. As has been stated previously, suture(s)/flexible member(s) are beneficially isolated from both the path of installer 510 and from the protrusions 605.

Figure 7:
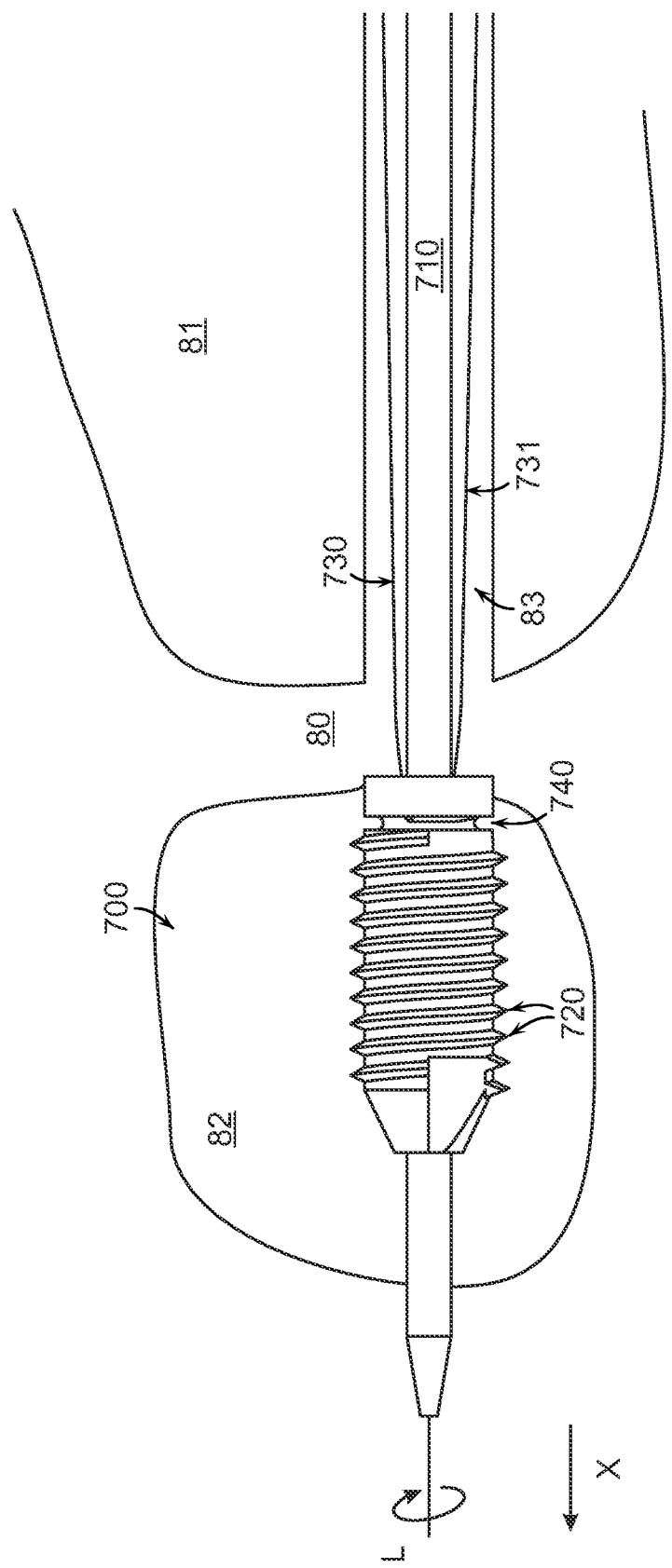
FIG. 7 depicts an embodiment of the cannulated anchor traversing a first bone and an intra-articular space for engaging in a second bone.

FIG. 7 illustrates a cannulated anchor of the "screw-in" variety. Guidewire 710 is passed through a first bone 81, through intra-articular space 80 and, subsequently, into second bone 82. As discussed in previous embodiments, anchor 700 and installer (not shown) are engaged with guidewire 710 to facilitate accurate placement and alignment of the resulting installed anchor based upon previous guidewire placement and alignment. Cannulated anchor 700 is advanced in the x direction along guidewire 710 by rotational movement of the installer about axis L. Helical threads 720 are effective in cutting tissue orifice 83. Alternatively, a drill (not shown) may be used to prepare a tissue orifice for passage of a cannulated anchor through a bone. Helical threads 720 are effective for securing cannulated anchor 700 with second bone 82. The "screw-in" variety provides a preferable method of engagement with bone over the "pound-in" anchor variety when traversing a first bone and intra-articular space to engage an anchor in a second bone. Sutures/flexible members 730 and 731 are isolated from the tissue orifice and external features of the anchor and do not interfere with the driver head of the installer due to the location of the suture channels (not shown) and circumferential recess 740 within the inner core anchor portion of cannulated anchor 700. Guidewire 710 may be removed from the tissue in either direction along x. Sutures 730 and 731 extend from the trailing end of anchor 700 and through the surgical insertion site (not shown), thereby made available to the surgeon for tensioning and affixing to tissue, graft, or other implant.

Although various exemplary embodiments of the invention have been disclosed, it should be apparent to those skilled in the art that various changes and modifications might be made that will achieve some of the disclosed advantages without departing from the true scope of the invention. These and other obvious modifications are intended to be covered by the appended claims.

What is claimed is:

1. An essentially cylindrical inner core anchor portion as part of a system for installing at least one flexible member into tissue, the inner core anchor portion having an inner core exterior wall and having an inner core length defined along a longitudinal system axis, the inner core length extending between a leading end and a trailing end, the inner core anchor portion comprising:
- a cannulation centrally disposed along the axis, the cannulation sized to accept a guidewire therethrough along the inner core length, the cannulation sized to engage an installer therethrough along a trailing portion of the inner core length;
- at least one recess disposed circumferentially within the inner core exterior wall, the at least one recess sized to accept a recess portion of the at least one flexible member; and
- a plurality of channels, each channel disposed essentially along the axis, each channel extending from the trailing end and in communication with the at least one recess, each channel sized to accept a channel portion of the at least one flexible member.

2. The inner core anchor portion of claim 1 wherein the plurality of channels are isolated from the cannulation along the trailing portion of the inner core length.

3. The inner core anchor portion of claim 1 wherein the at least one recess has a recess arc length measurable in circumferential degrees about the inner core anchor portion.

4. The inner core anchor portion of claim 3 wherein the recess arc length is 360 degrees.

5. The inner core anchor portion of claim 1 wherein the at least one recess is sized to accept a knotted portion of the at least one flexible member.

6. A cannulated anchor as part of a system for installing at least one flexible member into tissue, the anchor comprising:
- an essentially cylindrical inner core anchor portion having an inner core exterior wall and having an inner core length defined along a longitudinal system axis, the inner core length extending between a leading end and a trailing end, the inner core anchor portion comprising:
  - a cannulation centrally disposed along the axis, the cannulation sized to accept a guidewire therethrough along the inner core length, the cannulation sized to engage an installer therethrough along a trailing portion of the inner core length;
  - at least one recess disposed circumferentially within the inner core exterior wall, the at least one recess sized to accept a recess portion of the at least one flexible member; and
  - a plurality of channels, each channel disposed essentially along the axis, each channel extending from the trailing end and in communication with the at least one recess, each channel sized to accept a channel portion of the at least one flexible member; and
- an outer anchor portion having an outer length defined along the system axis and having an outer surface;

such that the outer surface is capable of effecting anchoring of the cannulated anchor into the tissue.

7. The cannulated anchor of claim 6 wherein the plurality of channels are isolated from the cannulation along the trailing portion of the inner core length.

8. The cannulated anchor of claim 6 wherein the outer anchor portion further comprises:
- a plurality of helical ribs, each rib disposed at a particular outer length position, each outer length position disposed between a first axial location proximate to the trailing end and a second axial location proximate to the leading end.

9. The cannulated anchor of claim 8 wherein the plurality of helical ribs are configured to provide threaded engagement with bone.

10. The cannulated anchor of claim 6 wherein a trailing profile of the cannulation that is disposed along the trailing portion of the inner core length is sized and dimensioned for matching with a driver head of the installer.

11. The cannulated anchor of claim 10 wherein the trailing profile is hexagonal.

12. The cannulated anchor of claim 10 wherein each of the plurality of channels is aligned with a trailing feature.

13. The cannulated anchor of claim 6 wherein the at least one recess has a recess arc length measurable in circumferential degrees about the inner core anchor portion.

14. The cannulated anchor of claim 12 wherein the recess arc length is at least 180 degrees.

15. The cannulated anchor of claim 13 wherein the recess arc length is 360 degrees.

16. The cannulated anchor of claim 12 wherein the recess arc length is less than 10 degrees and wherein the at least one recess is sized to accept a knotted portion of the at least one flexible member.

17. The cannulated anchor of claim 6 wherein a portion of the anchor is radio-opaque.

18. The cannulated anchor of claim 6 wherein a portion of the anchor has a porous coating to enhance osseointegration.

19. The cannulated anchor of claim 6 having a maximum anchor diameter, the maximum anchor diameter larger than an inner core anchor portion diameter; such that the outer surface is capable of effecting anchoring into tissue by application of force essentially along the axis.

20. The cannulated anchor of claim 19 wherein the maximum anchor diameter is measured from the system axis to the outer surface, the outer surface comprising at least one radial protrusion.

21. A system for installing at least one flexible member into tissue, the system comprising:
- the cannulated anchor of claim 6;
- the at least one flexible member capable of being received by the cannulated anchor; and
- an installer having a driver head insertable into the cannulation of the anchor proximate the trailing end, the installer having an essentially longitudinal installer cannulation centrally disposed along the axis sized to accept a guidewire therethrough;

wherein movement of the installer about the longitudinal axis causes corresponding movement of the cannulated anchor; such that the outer surface of the cannulated anchor is capable of effecting anchoring into the tissue.

22. A system for installing at least one flexible member into tissue, the system comprising:
- the cannulated anchor of claim 10;
- the at least one flexible member capable of being received by the cannulated anchor; and
- an installer having a driver head insertable into the cannulation of the anchor proximate the trailing end, the installer having an essentially longitudinal installer cannulation centrally disposed along the axis sized to accept a guidewire therethrough;

wherein movement of the installer about the longitudinal axis causes corresponding movement of the cannulated anchor; such that the outer surface of the cannulated anchor is capable of effecting anchoring into the tissue.

23. A method for installing at least one flexible member into tissue, the method comprising:
- inserting a guidewire into the tissue;
- providing the system of claim 21;
- engaging the installer with the anchor;
- positioning the anchor and the installer over the guidewire; and moving the installer causing corresponding movement of the anchor, such that the outer surface of the cannulated anchor is capable of effecting anchoring into the tissue.

24. A method for installing at least one flexible member across a first bone, across an intra-articular space, and into a second bone, the method comprising:
  inserting a guidewire into the first bone;
  advancing the guidewire across the intra-articular space into the second bone;
  providing the system of claim 21;
  engaging the installer with the anchor;
  positioning the cannulated anchor and the installer over the guidewire;
  moving the installer causing corresponding movement of the anchor; and
  moving the anchor across the intra-articular space into the second bone,
such that the outer surface of the cannulated anchor is capable of effecting anchoring into the second bone.

25. A method according to claim 23 wherein the outer surface is configured for threaded engagement with tissue and wherein moving the installer comprises rotating the installer to engage, advance, and anchor the cannulated anchor within the tissue.

26. A method according to claim 24 wherein the outer surface is configured for threaded engagement with bone and wherein moving the installer comprises rotating the installer to engage and advance the cannulated anchor within the bone.

27. The cannulated anchor of claim 6 wherein the at least one recess is sized to accept a knotted portion of the at least one flexible member.

28. A system for installing at least one flexible member into tissue, the system comprising:
  the cannulated anchor of claim 15;
  the at least one flexible member capable of being received by the cannulated anchor; and
  an installer having a driver head insertable into the cannulation of the anchor proximate the trailing end, the installer having an essentially longitudinal installer cannulation centrally disposed along the axis sized to accept a guidewire therethrough;
wherein movement of the installer about the longitudinal axis causes corresponding movement of the cannulated anchor; such that the outer surface of the cannulated anchor is capable of effecting anchoring into the tissue.

29. A system for installing at least one flexible member into tissue, the system comprising:
  the cannulated anchor of claim 27;
  the at least one flexible member capable of being received by the cannulated anchor; and
  an installer having a driver head insertable into the cannulation of the anchor proximate the trailing end, the installer having an essentially longitudinal installer cannulation centrally disposed along the axis sized to accept a guidewire therethrough;
wherein movement of the installer about the longitudinal axis causes corresponding movement of the cannulated anchor; such that the outer surface of the cannulated anchor is capable of effecting anchoring into the tissue.

30. A cannulated anchor, as part of a system for anchoring at least one flexible member into tissue, the system having a defined longitudinal axis, the at least one flexible member loaded substantially along the axis, the at least one flexible member comprising a channel member portion, a recess member portion and a free member portion, the free member portion having at least one graspable free end, the anchor comprising:
  an essentially cylindrical inner core anchor portion having an inner core exterior wall and having an inner core length defined along the axis, the inner core length extending between a leading end and a trailing end, the inner core anchor portion comprising:
    a cannulation centrally disposed along the axis, the cannulation sized to accept a guidewire therethrough along the inner core length, the cannulation sized to engage an installer therethrough along a trailing portion of the inner core length;
    at least one recess disposed circumferentially within the inner core exterior wall, the at least one recess sized to accept the recess member portion;
    a plurality of channels, each channel disposed essentially along the axis, each channel extending from the trailing end and in communication with the at least one recess, each channel sized to accept the channel member portion; and
  an outer anchor portion having an outer length defined along the system axis and having an outer surface;
such that the outer surface is capable of effecting anchoring of the cannulated anchor into the tissue.

31. The cannulated anchor of claim 30 wherein the plurality of channels are isolated from the cannulation along the trailing portion of the inner core length.

32. The cannulated anchor of claim 30 wherein a trailing profile of the cannulation that is disposed along the trailing portion of the inner core length is sized and dimensioned for matching with a driver head of the installer.

33. The cannulated anchor of claim 32 wherein the trailing profile is hexagonal.

34. The cannulated anchor of claim 32 wherein each of the plurality of channels is aligned with a trailing feature.

35. The cannulated anchor of claim 30 wherein the at least one recess has a recess arc length measurable in circumferential degrees about the inner core anchor portion.

36. The cannulated anchor of claim 35 wherein the recess arc length is 360 degrees.

37. The cannulated anchor of claim 30 wherein a portion of the anchor is radio-opaque.

38. The cannulated anchor of claim 30 wherein a portion of the anchor has a porous coating to enhance osseointegration.

39. The cannulated anchor of claim 30 having a maximum anchor diameter, the maximum anchor diameter larger than an inner core anchor portion diameter; such that the outer surface is capable of effecting anchoring into tissue by application of force essentially along the axis.

40. An essentially cylindrical inner core anchor portion of a cannulated anchor as part of a system for anchoring at least one flexible member into tissue, the system having a defined longitudinal axis, the at least one flexible member loaded substantially along the axis, the at least one flexible member comprising a channel member portion, a recess member portion and a free member portion, the free member portion having at least one graspable free end, the inner core anchor portion having an inner core exterior wall and having an inner core length defined along the axis, the inner core length extending between a leading end and a trailing end, the inner core anchor portion comprising:
  a cannulation centrally disposed along the axis, the cannulation sized to accept a guidewire therethrough along the inner core length, the cannulation sized to engage an installer therethrough along a trailing portion of the inner core length;
  at least one recess disposed circumferentially within the inner core exterior wall, the at least one recess sized to accept the recess member portion; and a plurality of channels, each channel disposed essentially along the axis, each channel extending from the trailing end and in communication with the at least one recess, each channel sized to accept the channel member.

41. A system for installing at least one flexible member into tissue, the system comprising:
the cannulated anchor of claim 30;
the at least one flexible member capable of being received by the cannulated anchor; and
an installer having a driver head insertable into the cannulation of the anchor proximate the trailing end, the installer having an essentially longitudinal installer cannulation centrally disposed along the axis sized to accept a guidewire therethrough;
wherein movement of the installer about the longitudinal axis causes corresponding movement of the cannulated anchor; such that the outer surface of the cannulated anchor is capable of effecting anchoring into the tissue.

42. The system of claim 41, the at least one flexible member having a member length and a recess member portion length, each channel having a channel length, such that the member length is longer than twice the channel length plus the recess member portion length, wherein the at least one flexible member slidingly engages with the cannulated anchor, resulting in the free member portion having two graspable free ends.

43. A system for installing at least one flexible member into tissue, the system comprising:
the cannulated anchor of claim 32;
the at least one flexible member capable of being received by the cannulated anchor; and
an installer having a driver head insertable into the cannulation of the anchor proximate the trailing end, the installer having an essentially longitudinal installer cannulation centrally disposed along the axis sized to accept a guidewire therethrough;
wherein movement of the installer about the longitudinal axis causes corresponding movement of the cannulated anchor; such that the outer surface of the cannulated anchor is capable of effecting anchoring into the tissue.

44. The inner core anchor portion of claim 40 wherein the plurality of channels are isolated from the cannulation along the trailing portion of the inner core length.

45. The inner core anchor portion of claim 40 wherein the at least one recess has a recess arc length measurable in circumferential degrees about the inner core anchor portion.

46. The inner core anchor portion of claim 45 wherein the recess arc length is 360 degrees.

47. The cannulated anchor of claim 30 wherein the at least one recess is sized to accept a knotted portion of the at least one flexible member.

48. The inner core anchor portion of claim 40 wherein the at least one recess is sized to accept a knotted portion of the at least one flexible member.

49. A system for installing at least one flexible member into tissue, the system comprising:
the cannulated anchor of claim 36;
the at least one flexible member capable of being received by the cannulated anchor; and
an installer having a driver head insertable into the cannulation of the anchor proximate the trailing end, the installer having an essentially longitudinal installer cannulation centrally disposed along the axis sized to accept a guidewire therethrough;
wherein movement of the installer about the longitudinal axis causes corresponding movement of the cannulated anchor; such that the outer surface of the cannulated anchor is capable of effecting anchoring into the tissue.

50. A system for installing at least one flexible member into tissue, the system comprising:
the cannulated anchor of claim 47;
the at least one flexible member capable of being received by the cannulated anchor; and
an installer having a driver head insertable into the cannulation of the anchor proximate the trailing end, the installer having an essentially longitudinal installer cannulation centrally disposed along the axis sized to accept a guidewire therethrough;
wherein movement of the installer about the longitudinal axis causes corresponding movement of the cannulated anchor; such that the outer surface of the cannulated anchor is capable of effecting anchoring into the tissue.

* * * * *

UNITED STATES PATENT AND TRADEMARK OFFICE
CERTIFICATE OF CORRECTION

Page 1 of 1

PATENT NO. : 8,679,168 B2
APPLICATION NO. : 12/395891
DATED : March 25, 2014
INVENTOR(S) : Michael G. McNamara et al.

It is certified that error appears in the above-identified patent and that said Letters Patent is hereby corrected as shown below:

In the Specification:
At column 1, line 25, following "used" add "in"
At column 3, line 6, following "still" add "be"
At column 3, line 22, replace "osseointegration" with "osseointegration."
At column 5, line 24, replace "fact" with "fact,"
At column 7, line 22, following "torquing" add "the"
At column 7, line 42, replace "510," with "510"
At column 7, line 51, replace "members" with "member(s)"

In the Claims:
At column 10, line 12, claim 14, replace "claim 12" with "claim 13"
At column 10, line 16, claim 16, replace "claim 12" with "claim 13"
At column 12, line 13, claim 30, following "portion;" add "and"

Signed and Sealed this
Twenty-fourth Day of June, 2014

Michelle K. Lee
*Deputy Director of the United States Patent and Trademark Office*